United States Patent [19]
Mizukami et al.

[11] Patent Number: 5,587,106
[45] Date of Patent: Dec. 24, 1996

[54] LIQUID CRYSTAL DISPLAY DEVICES AND LIQUID CRYSTAL SUBSTANCES THEREFOR

[75] Inventors: Masamichi Mizukami, Tsukuba; Tomoyuki Yui, Nagareyama; Yoshihisa Arai; Yoshihiro Gocho, both of Tsukuba, all of Japan

[73] Assignee: Mitsubishi Gas Chemical Company, Inc., Tokyo, Japan

[21] Appl. No.: 467,898

[22] Filed: Jun. 6, 1995

Related U.S. Application Data

[63] Continuation of Ser. No. 52,604, Apr. 27, 1993, abandoned.

[30] Foreign Application Priority Data

Apr. 27, 1992 [JP] Japan ................... 4-107529

[51] Int. Cl.$^6$ .................. C09K 19/34; C07D 239/02; G02F 1/13
[52] U.S. Cl. .................. 252/299.61; 544/298; 349/182
[58] Field of Search .................. 252/299.61; 544/298; 359/103

[56] References Cited

U.S. PATENT DOCUMENTS

| | | | |
|---|---|---|---|
| 4,918,213 | 4/1990 | Nohira et al. | 558/271 |
| 4,921,632 | 1/1990 | Nakamura et al. | 252/299.1 |
| 5,089,168 | 2/1992 | Krause et al. | 252/299.61 |
| 5,110,496 | 5/1992 | Mogamiya et al. | 252/299.61 |
| 5,202,054 | 4/1993 | Suzuki et al. | 252/299.61 |
| 5,211,879 | 5/1993 | Shiratori | 252/299.67 |
| 5,238,603 | 8/1993 | Miyazawa et al. | 252/299.65 |
| 5,275,757 | 1/1994 | Mineta et al. | 252/299.61 |
| 5,281,362 | 1/1994 | Nohira et al. | 252/299.61 |

FOREIGN PATENT DOCUMENTS

| | | |
|---|---|---|
| 0267585 | 5/1988 | European Pat. Off. |
| 0445037 | 4/1991 | European Pat. Off. |
| 228862 | 11/1990 | Japan |
| 429978 | 1/1992 | Japan |
| 446158 | 2/1992 | Japan |
| 6145111 | 5/1994 | Japan |

OTHER PUBLICATIONS

Database WPI Derwent Publications Ltd., London, GB; AN 92–085891 & JPA 4 029 978 (Mitsubishi Petrochem.) 13 Jan. 1992.
Database WPI Derwent Publications, Ltd., London, GB; AN 87–224864 & JPA 62–149 669 (Toray Ind Inc) 3 Jul. 1987.
Patent Abstracts of Japan vol. 016, No. 234 (C–945) 29 May 1992 & JPA 40 46 158 (Mitsubishi Petrochem Co) 17 Feb. 1992.
Japanese Journal of Applied Physics vol. 29, No. 6/2, Jun. 1990, Tokyo JP pp. L987–L990.
Japanese Journal of Applied Physics vol. 30, No. 6A, 1 Jun. 1991, Tokyo JP pp. L1032–L1035.

*Primary Examiner*—C. H. Kelly
*Attorney, Agent, or Firm*—Sherman and Shalloway

[57] ABSTRACT

Anti-ferroelectric liquid crystal substances which are represented by the formula (1):

$$R-O-\phi-(N\!=\!\!=\!\!N)-COO-\phi(X)-COO-C^{**}H(Z)(CH_2)_l(O)_m C_n H_{2n+1} \quad (1)$$

wherein
R is a straight chain alkyl group having 6 to 10 carbon atoms,
X is hydrogen or fluorine atom,
Z is —CH$_3$, —CF$_3$ or —C$_2$H$_5$, and
C** stands for an asymmetric carbon atom, and
l, m, and n are 0 or a certain integer depending on the specific kinds of X and Z,
and the use of the substances for liquid crystal display devices.

9 Claims, 15 Drawing Sheets

LIQUID CRYSTAL DISPLAY DEVICES AND LIQUID CRYSTAL SUBSTANCES THEREFOR

This is a continuation under 37 CFR 1.62 of applicants' prior application Ser. No. 08/052,604 filed Apr. 27, 1993 abandoned.

INDUSTRIALLY APPLICABLE FIELD

This invention relates to liquid crystal display devices and liquid crystal substances therefor. More specifically, this invention relates to anti-ferroelectric liquid crystal substances such as pyrimidine, and liquid crystal display devices in which such substances are used.

PRIOR ART

Liquid crystal display devices have been so far used in various small-size display devices, because of their favorable characteristics such as operability at low voltages, low electric power consumption and display capability with a thin screen. With the recent increase in application and use of a liquid display device, for example, to/in the fields of information and office automation equipment or the television field, demands for high performance, large-size liquid crystal display devices having a larger display capacity and a higher quality than those of conventional CRT display devices have rapidly been increasing.

However, so long as the presently available nematic liquid crystals are used, even the active matrix-driven liquid crystal display devices which are currently used for liquid crystal televisions find it difficult to enlarge the device size and reduce the production cost, due to the complexity in their production process and low yield. Further, even with simple matrix-driven STN-type liquid crystal display devices, the driving of a display having a large capacity is not necessarily easy. Furthermore, there is limitation also in response time, and it is difficult to display video rate. Thus, it is the present state of art that a nematic liquid crystal display device hardly satisfy the above demands for a high performance and larger-size crystal display device.

Problems to be Solved by the Invention

On the other hand, a liquid crystal display device using a ferroelectric liquid crystal substance is drawing attention as a liquid crystal display device with high speed response. A surface-stabilized ferroelectric liquid crystal (SSFLC) device proposed by N. A. Clark and S. T. Lagerwall is attracting attention to its unprecedented high speed of response and wide visual angle [N. A. Clark and S. T. Lagerwall, Appl. Phys. Lett. 36 (1980) 899].

Switching characteristics of this SSFLC have detailedly been studied, and many ferroelectric liquid crystal substances have been synthesized to optimize various physical property parameters. There are still various problems, however, such as insufficient threshold characteristics; unsatisfactory contrast ascribed to chevron structure of the liquid crystal layer, incompleteness of high speed response; difficulty in controlling molecular alignment of liquid crystals, which leads to the difficulty in attaining bistability which is one of the most prominent characteristics of SSFLC, tendency of the liquid crystal molecular alignment to be destroyed by mechanical impact and difficulty in recovering the destroyed alignment, etc. Because of those negative factors, SSFLC devices have not yet been reduced to practical use.

Separately therefrom, development of devices having a switching mechanism different from that of SSFLC is being advanced at the same time. Switching in tristable states of a liquid crystal substance having an anti-ferroelectric phase (hereafter referred to as an anti-ferroelectric liquid crystal substance) is one of these new switching mechanisms (refer to Japanese Journal of Applied Physics, Vol. 27, pp. L729, 1988). An anti-ferroelectric liquid crystal substance has three stable states, i.e., the two uniform states (Ur, Ul) which are observed in a ferroelectric liquid crystal substance and the third state.

Chandani, et al. report that this third state is the anti-ferroelectric phase (refer to Japanese Journal of Applied Physics, vol. 28, pp. L1261 and L1265, 1989). Such switching in tristable states is the first characteristic of an anti-ferroelectric liquid crystal substance. The second characteristic of an anti-ferroelectric liquid crystal substance is that it has a distinct threshold value for applied voltage. The third characteristic of an anti-ferroelectric liquid crystal substance is that it has good memory effect. By using an anti-ferroelectric liquid crystal substance having these excellent characteristics, it is possible to work out a liquid crystal display device giving quick response and good contrast.

Still another notable characteristic of an anti-ferroelectric liquid crystal substance is that its layer structure can be readily switched by an electric field (Japanese Journal of Applied Physics, vol. 28, pp. L119, 1989 and Japanese Journal of Applied Physics, vol. 29, L111, 1990). It becomes thereby possible to make a liquid crystal display device having very few defects in the liquid crystal layer and having an ability to self-restore the molecular alignment, and it is possible to realize a liquid crystal display device excellent in contrast.

As anti-ferroelectric liquid crystal substances, known are those disclosed in Japanese Laid-Open Patent Publication Nos. 213,390/1989, 316,339/1989, 316,367/1989, 316,372/1989 and 28,128/1990 and *Liquid Crystals*, vol. 6, pp. 167, 1989. Since the history of studies on anti-ferroelectric liquid crystal substances is short, the number of anti-ferroelectric liquid crystal substances so far known is not large compared to ferroelectric liquid crystal substances, but the number is gradually increasing with the advance in their research work.

As already stated, the layer structure of anti-ferroelectric liquid crystal substances is apt to take a book-shelf structure when voltage is applied. This strongly suggests that the substances would provide liquid display devices having excellent contrast. Nevertheless, judging from practical standpoint, heretofore synthesized anti-ferroelectric liquid crystal substances are mostly insufficient in contrast. This is mainly attributable to their poor molecular alignment and many defects in the layer. Therefore, it is presumed that in concert with the tendency to assume the book-shelf structure under applied voltage, liquid crystal substance of good molecular alignment would provide an excellent material to produce good contrast. The present invention has been worked out to meet the above strong demand, based on the foregoing assumption, and is to provide liquid crystal substances of excellent alignment and liquid crystal display devices in which such substances are used.

The first object of the present invention is, therefore, to provide novel liquid crystal substances having anti-ferroelectric property.

The second object of the invention is to provide liquid crystal substances permitting switching in tristable states and having distinct threshold characteristics and good memory effect.

The third object of the invention is to provide liquid crystal substances having high speed of response and useful for large size liquid crystal display devices.

Another object of the invention is to provide liquid crystal substances excelling in molecular alignment and having high contrast ratio.

Still another object of the invention is to provide liquid crystal display devices in which the above liquid crystal substances exhibiting such excellent characteristics are used.

Further objects and advantages of the invention will become apparent from the following description.

Means for Solving the Problems

According to researches by the present inventors, the above objects and advantages of this invention can be attained by the provision of anti-ferroelectric liquid crystal substances represented by the following formula (1)

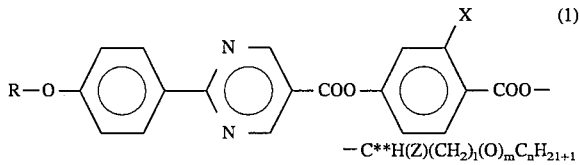

$-C^{**}H(Z)(CH_2)_l(O)_mC_nH_{2l+1}$ wherein

R is a straight chain alkyl group having 6 to 10 carbon atoms,

X is hydrogen or fluorine atom,

Z is —$CH_3$, —$CF_3$ or —$C_2H_5$, and

C** stands for an asymmetric carbon atom, with the provisos that (i) when X is hydrogen atom and Z is —$CH_3$, l is O or an integer of 5 to 8, m is O or 1and n is an integer of 1 to 10; or (ii) when X is hydrogen atom and Z is —$CF_3$, l is an integer of 5 to 8, m is 1, and n is an integer of 1 to 10; or (iii) when X is fluorine atom, Z is —$CH_3$, —$CF_3$ or —$C_2H_5$, l is O or an integer of 5 to 8, m is 0 or 1, and n is an integer of 1 to 10.

The liquid crystal substance represented by the above formula (1) of the present invention and its use as a liquid crystal display device will be explained in detail hereinbelow.

In the formula (1), R stands for a straight chain alkyl group having 6 to 10 carbon atoms, preferably an alkyl group having 8 carbon atoms (n-octyl).

X stands for hydrogen or fluorine atom, Z stands for —$CH_3$, —$CF_3$ or —$C_2H_5$, and C** stands for an asymmetric carbon atom. The definitions of l, m and n vary depending on specific combination of X and Z, i.e., (i) when X is hydrogen atom and Z is —$CH_3$ l is 0 or an integer of 5 to 8, m is 0 or 1, and n is an integer of 1 to 10; preferably both l and m are 0 and n is an integer of 6 to 10, or l is an integer of 5 to 7, m is 1 and n is 2;

(ii) When X is hydrogen atom and Z is —$CF_3$ l is an integer of 5 to 8; m is 1 and n is an integer of 1 to 10; preferably is an integer of 5 to 7, m is 1 and n is 2;

(iii) When X is fluorine atom Z is any of —$CH_3$, —$CF_3$ and —$C_2H_5$, l is 0 or an integer of 5 to 8, m is 0 or 1 and n is an integer of 1 to 10; preferably, when Z is —$CH_3$, both l and m are 0 and n is an integer of 6 to 10; or l is an integer of 5 to 7, m is 1 and n is 2; when Z is —$CF_3$, both l and m are 0 and n is an integer of 6 to 8; or l is an integer of 5 to 7, m is 1 and n is 2; when Z is —$C_2H_5$, both l and m are 0 and n is 6. The compounds represented by the formula (1) can be prepared by various synthesis methods. One example of the synthesis methods is shown hereafter by means of a reaction formula in which R, X, Z, l, m, n and C** have the same meanings as above, and Et means an ethyl group.

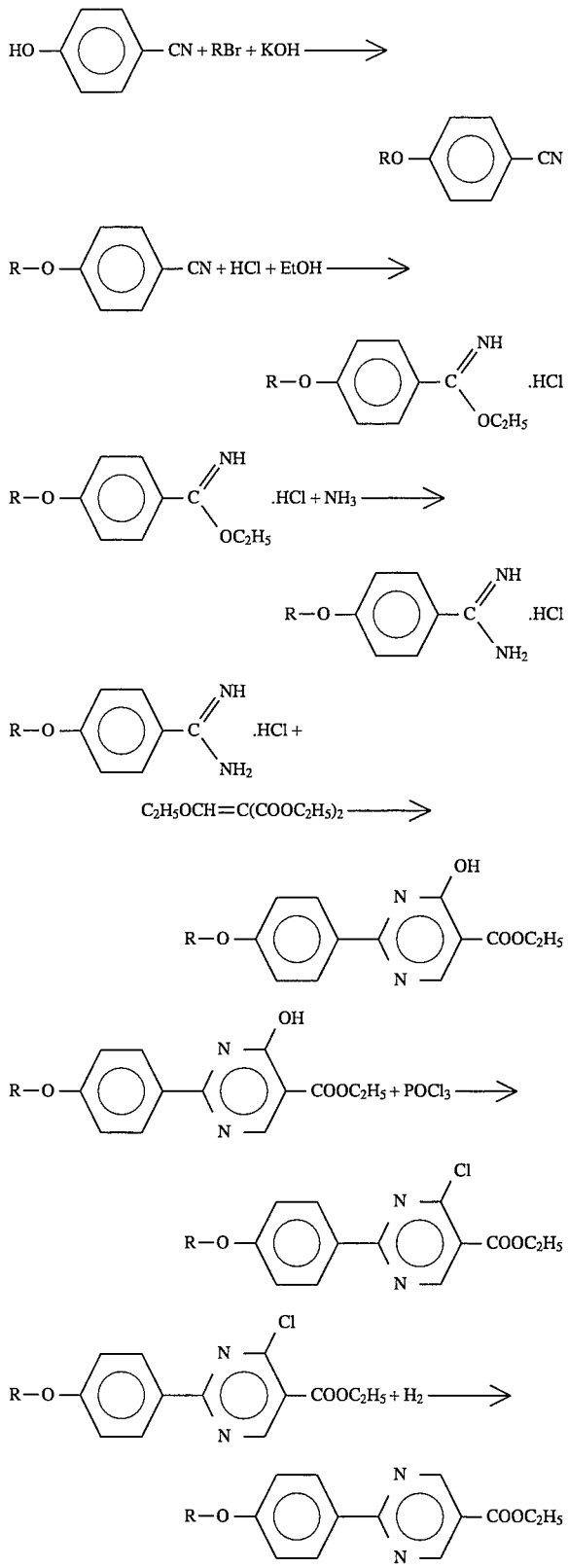

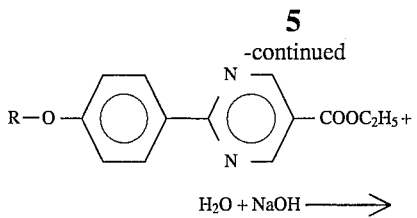
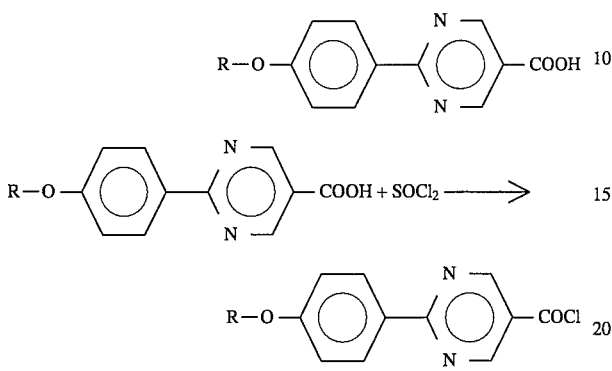

<Compound A>;

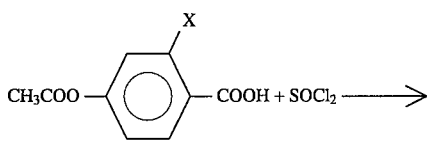
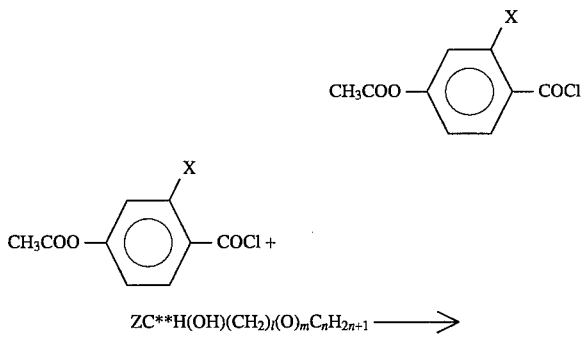
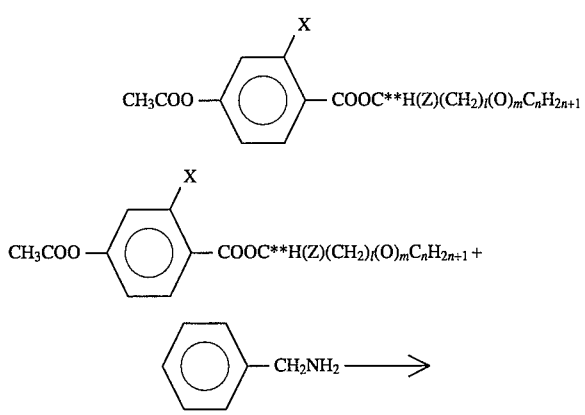
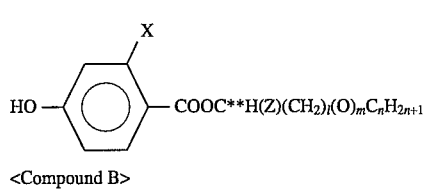

<Compound B>

<Compound A> + <Compound B> ⟶
the object compound of the formula (1)

4-Acetoxy-2-fluorobenzoic acid (when X is fluorine atom), which is used as the starting material for the synthesis of Compound B in the above reaction formulae, can be synthesized according to the following reaction formula, using, for example, m-fluorophenol as the starting material.

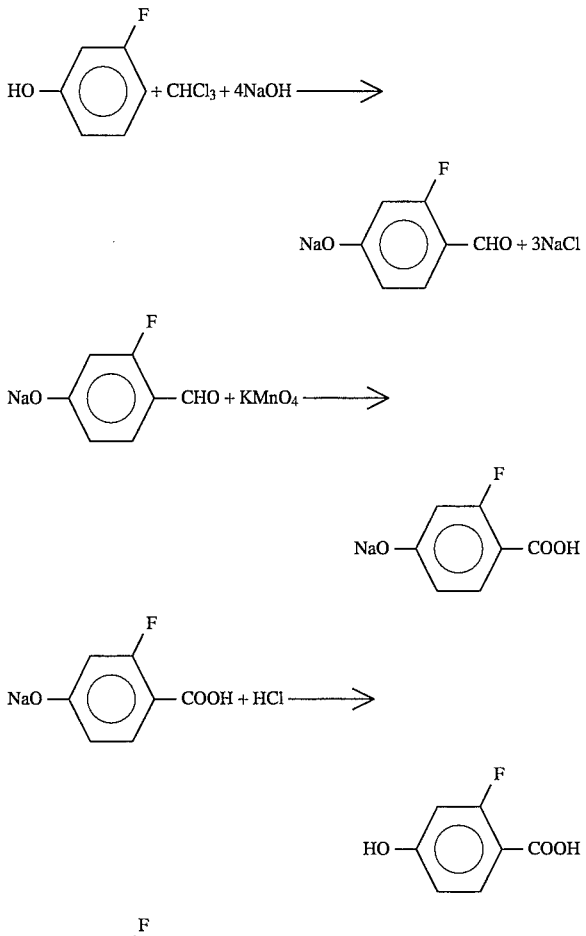

The compounds represented by the formula (1) of the present invention are novel and are anti-ferroelectric liquid crystal substances. Because the anti-ferroelectric substances of the present invention excel in alignment properties, they can provide liquid crystal display devices exhibiting high contrast ratio. The liquid crystal display devices are imparted with the characteristic properties of said substances such as high speed of response, switching in tristable states, distinct threshold characteristics and good memory effect. In particular, the liquid crystal substances of the present invention exhibit the contrast ratio of at least 10, and that of at least 13 in preferred embodiments.

"Contrast ratio" as referred to in the above is determined under the following measuring conditions.

Method of measuring contrast ratio

Between two orthogonal polarizing plates, a liquid crystal cell is placed such that its layer direction coincides with the direction of either one of the polarizing plates. A triangular wave voltage of ±40 V at a frequency of 50 mHz is applied to the liquid crystal cell, and the relationship between the applied voltage and the amount of transmitted light as illustrated in FIG. 15 is examined. For measuring the amount of transmitted light, a photomultipler is used.

Here the threshold voltages of U90 and D90 are defined as follows. Referring to the variation in transmitted light as indicated in FIG. 15, the transmitted light at the darkest condition is marked 0 % and that at the lightest condition, 100 %. In the course of the variation in transmitted light at switching from anti-ferroelectric state to ferroelectric state, the voltage at which the transmitted light reaches 90 % is defined to be U90. Similarly, in the variation in light transmission at switching from ferroelectric state to antiferroelectric state, the voltage at which the transmitted light reached 90 % is defined to be D90.

The ratio in lightness values between the two states (anti-ferroelectric state and ferroelectric state) at the mean voltage of U90 and D90 is taken as the contrast ratio. That is, the ratio of lightness values at point A in anti-ferroelectric state and point B in ferroelectric state is defined as the contrast ratio.

Figure 1:
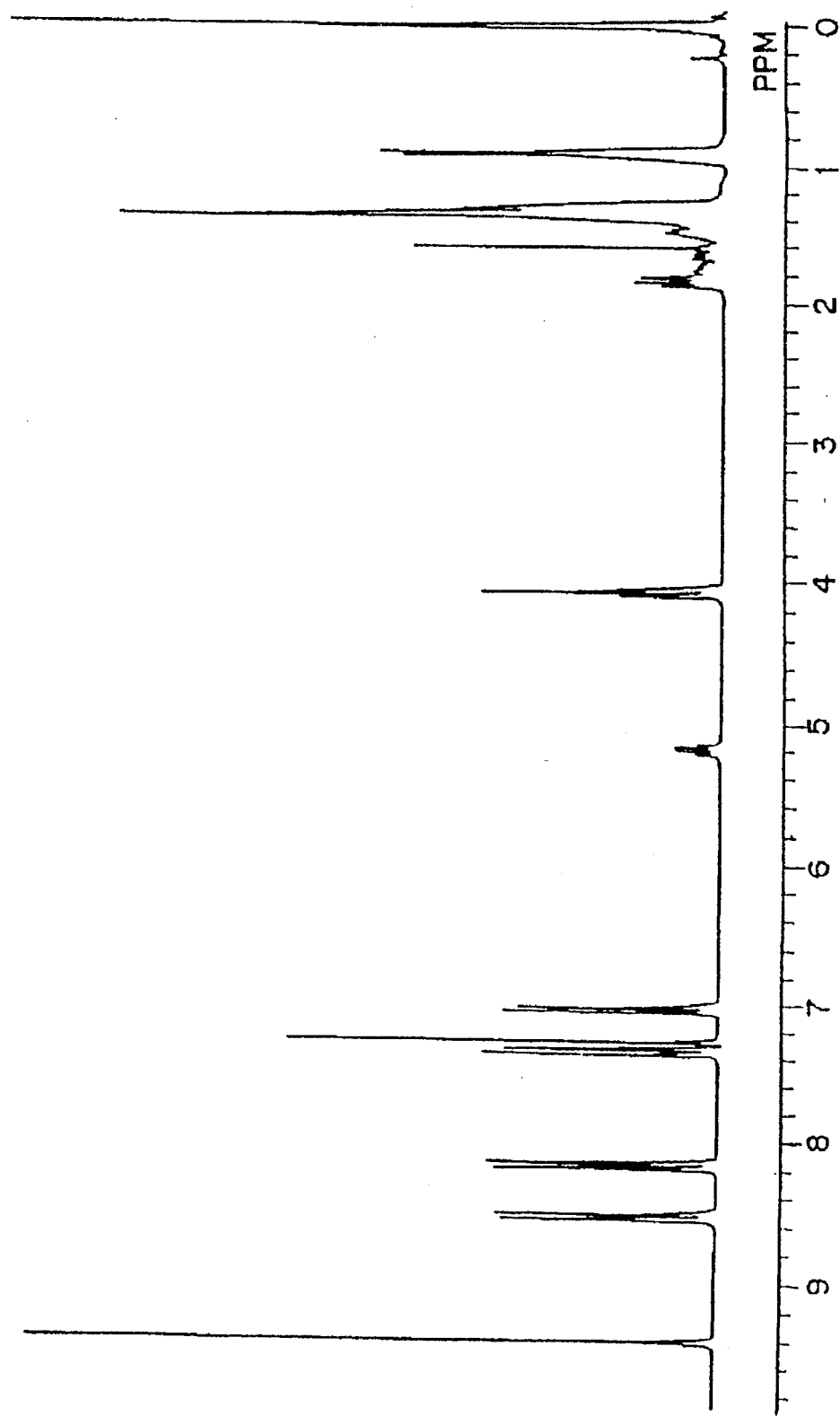
FIG. 1 is a drawing showing the NMR spectrum of the liquid crystal substance obtained in Example 1.

The invention is more specifically explained hereinafter, referring to working examples and comparative examples, it being understood that the invention is in no way limited thereto.

Example 1

Preparation of
4-(1-methylpentyloxycarbonyl)phenyl ester of
(R)-2-(4-octyloxyphenyl)-5-pyrimidine- carboxylic
acid [the case of $R=C_8H_{17}$, $X=H$, $Z=CH_3$, $l=0$,
$m=0$ and $n=4$ in the general formula (1)]

1) Preparation of 2-(4-octyloxyphenyl)-pyrimidine-5-carboxylic acid (1)

A 1-liter round bottom flask was charged with 50 g of p-hydroxybenzonitrile, 89.2 g of octyl bromide, 23.5 g of potassium hydroxide and 500 ml of ethanol. A calcium chloride tube was attached to the flask and the content was refluxed for 4 hours. Then, one liter of water was added into the flask, followed by extraction with 1300 ml of dichloromethane. The extract was washed with water and dried over anhydrous sodium sulfate. After distilling the solvent off, the remaining system was purified by means of silica gel column chromatography to provide 80.6 g of 4-octyloxybenzonitrile (Compound A).

Eleven (11) g of the above Compound A was dissolved in 80 ml of ethanol, and into the resultant solution hydrogen chloride gas was blown over 2 hours while cooling with ice. Thereafter the system was sealed hermetically and allowed to stand an overnight. Then, the hydrochloric acid and ethanol were distilled off from the reaction mixture under reduced pressure. To the solidified reaction mixture 120 ml of ethanol was added and stirred for a while to dissolve the reaction mixture. Into this reaction solution 40 ml of liquified ammonia was added under ice cooling, which procedure requiring 80 minutes. After completion of addition of ammonia, the system was sealed hermetically and allowed to stand an overnight. Thus, the amidine compound (Compound B) was formed.

The ammonia and ethanol were distilled off from the reaction solution containing above Compound B. To the pasty reaction product, 120 ml of fresh ethanol was added, followed by further addition of 6.5 g of metallic sodium under cooling with water. When most of the added metallic sodium disappeared, 20.5 g of diethyl ethoxymethylenemalonate was added to the system and stirred for 30 minutes at room temperature, followed by refluxing for 6 hours. The reaction solution was poured into water and extracted with chloroform. After drying the extract with sodium sulfate, the solvent was distilled off to provide crude 2-(4-octyloxyphenyl)-4-hydroxy-5ethoxycarbonylpyrimidine (Compound C). The crude product was recrystallized to provide 9.8 g of a purified Compound C.

Four (4) g of the above Compound C was mixed with 20 ml of phosphoryl chloride, and the mixture was refluxed for 30 minutes. Then, the phosphoryl chloride was recovered, and the residue was poured into water. After neutralization with potassium carbonate, the system was extracted with dichloromethane and the extract was dried with sodium sulfate. After distilling the solvent off, the extract was purified by means of column chromatography to provide 3.9 g of 2(4-octyloxyphenyl)-4-chloro-5-ethoxycarbonylpyrimidine (Compound D).

Six (6) g of hydrogenation catalyst in which 5 % of Pd was carried on activated carbon and a small amount of sodium acetate were placed in an eggplant-shaped flask.

After replacing the atmosphere inside the flask with nitrogen, 6 g of the above Compound D dissolved in 90 ml of dioxane was slowly dropped into the flask through a dropping funnel. After replacing the inside atmosphere with hydrogen with stirring, hydrogen was supplied from a gas reservoir. The reaction was continued until hydrogen absorption ceased. Thereafter the atmosphere was replaced with nitrogen, and the catalyst was removed by filtration. The solvent was recovered from the filtrate. Thus obtained crude product was purified by column chromatography and recrystallization to provide 6.1 g of purified 2-(4-octyloxyphenyl)-5- ethoxycarbonylpyrimidine (Compound E).

An eggplant type flask was charged with 2.6 g of the above Compound E, 0.8 g of potassium hydroxide, 45 ml of ethanol and 5 ml of water. The system was refluxed for one hour, and the resultant reaction liquid was poured into 100 ml of water, which was made acidic with hydrochloric acid and extracted with chloroform. The extract was dried over sodium sulfate, removed the solvent by distillation, and recrystallized with 50 ml of hexane. The crystalline product was recovered by filtration, and dried to provide 2.3 g of the object 2-(4-octyloxyphenyl)pyrimidine-5-carboxylic acid, which was the object product.

2) Preparation of 4-(1-methylpentyloxycarbonyl) phenyl ester of (R)-2-(4-octyloxyphenyl)-5-pyrimidinecarboxylic acid To 1 g of the 2-(4-octyloxyphenyl)- pyrimidine-5-carboxylic acid obtained in above 1), 20 ml of thionyl chloride was added, followed by refluxing for 6 hours. Thereafter, the excess thionyl chloride was distilled off. To the remaining system 10 ml of pyridine was added, and further, into which a solution of 0.6 g of (R)-(+)-4-hydroxy-l-(1methylpentyloxycarbonyl) benzene dissolved in 10 ml of toluene was added dropwise under stirring. Thereafter, the stirring was continued for a day and night. Water was added to the resultant reaction liquid, followed by extraction with dichloromethane. The liquid extract was washed with hydrochloric acid, aqueous caustic soda solution, and water, by the order stated, and dried with sodium sulfate. The solvent was distilled off, and the remaining crude product was purified by means of column chromatography to provide 0.6 g of the object product. The NMR spectrum of the product is shown as FIG. 1.

Phase identification of the object product was done by texture observation and DSC measurement. The melting point measurement was conducted with DSC, and the measured value was 110° C.

The phase sequence of this compound was as follows. An anti-ferroelectric phase was observed with this compound.

Figure 2:
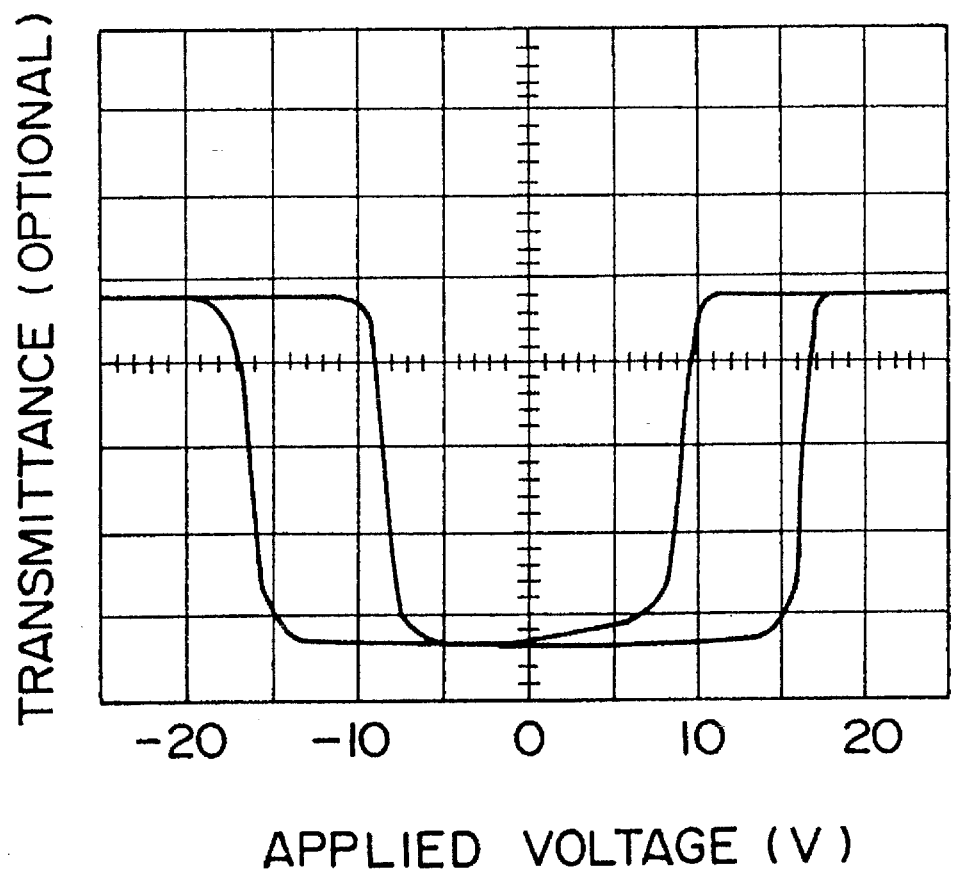
FIG. 2 is a drawing showing the optical response hysteresis of the liquid crystal substance obtained in Example 1.

3) The above compound in isotropic state was charged in a liquid crystal cell (cell thickness: 3 μm) having a rubbing-treated thin polyimide film and equipped with ITO electrodes. This cell was gradually cooled at a rate of 1.0° C. per minute thereby to align the liquid crystal in the SA phase. The cell was placed between orthogonal polarizing plates in such a manner that the layer direction of the liquid crystal paralleled the analyzer or the polarizer. A triangle wave voltage of ±40 V and 0.2 Hz was applied to the cell, and the variation in light transmission was measured by a photomultiplier. As a result, double response hysteresis peculiar to an anti-ferroelectric phase was recognized in the temperature region from 120° to 95° C. Optical response hysteresis at 90° C is shown in FIG. 2.

When the contrast ratio was measured at 90° C., it was as high as 15.

Examples 2, 3 and 4

Figure 3:
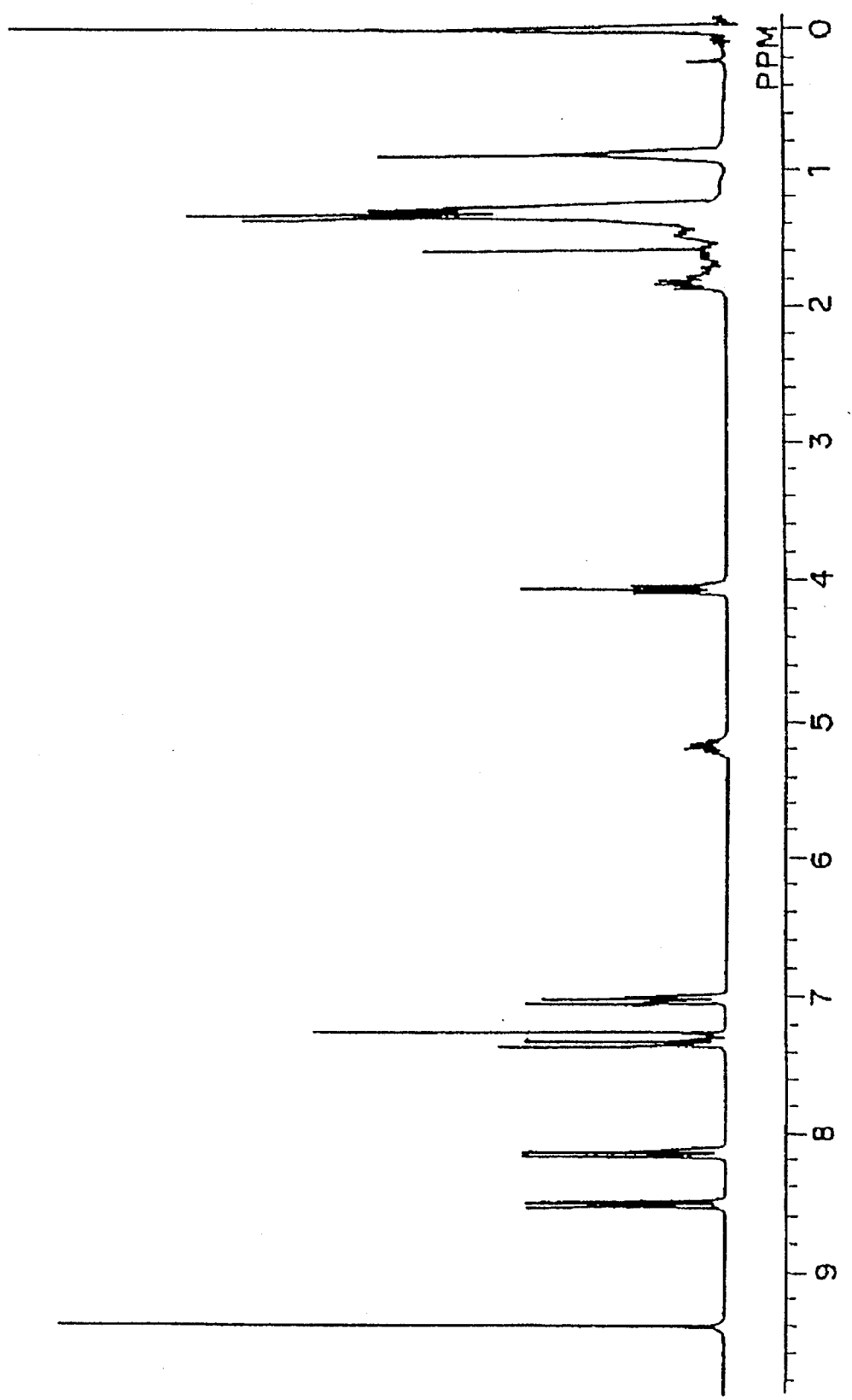
FIG. 3 is a drawing showing the NMR spectrum of the liquid crystal substance obtained in Example 2.
Figure 4:
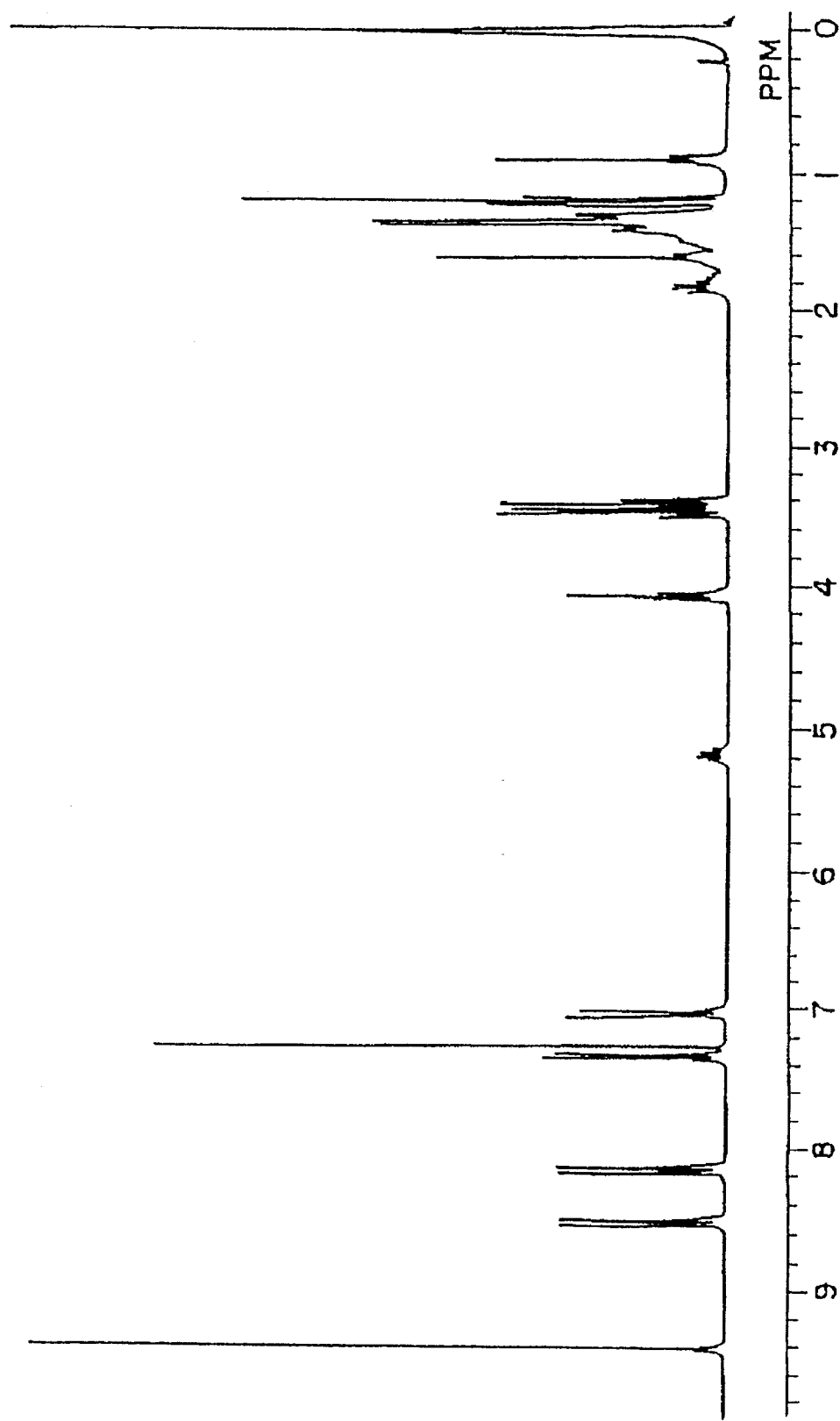
FIG. 4 is a drawing showing the NMR spectrum of the liquid crystal substance obtained in Example 3.
Figure 5:
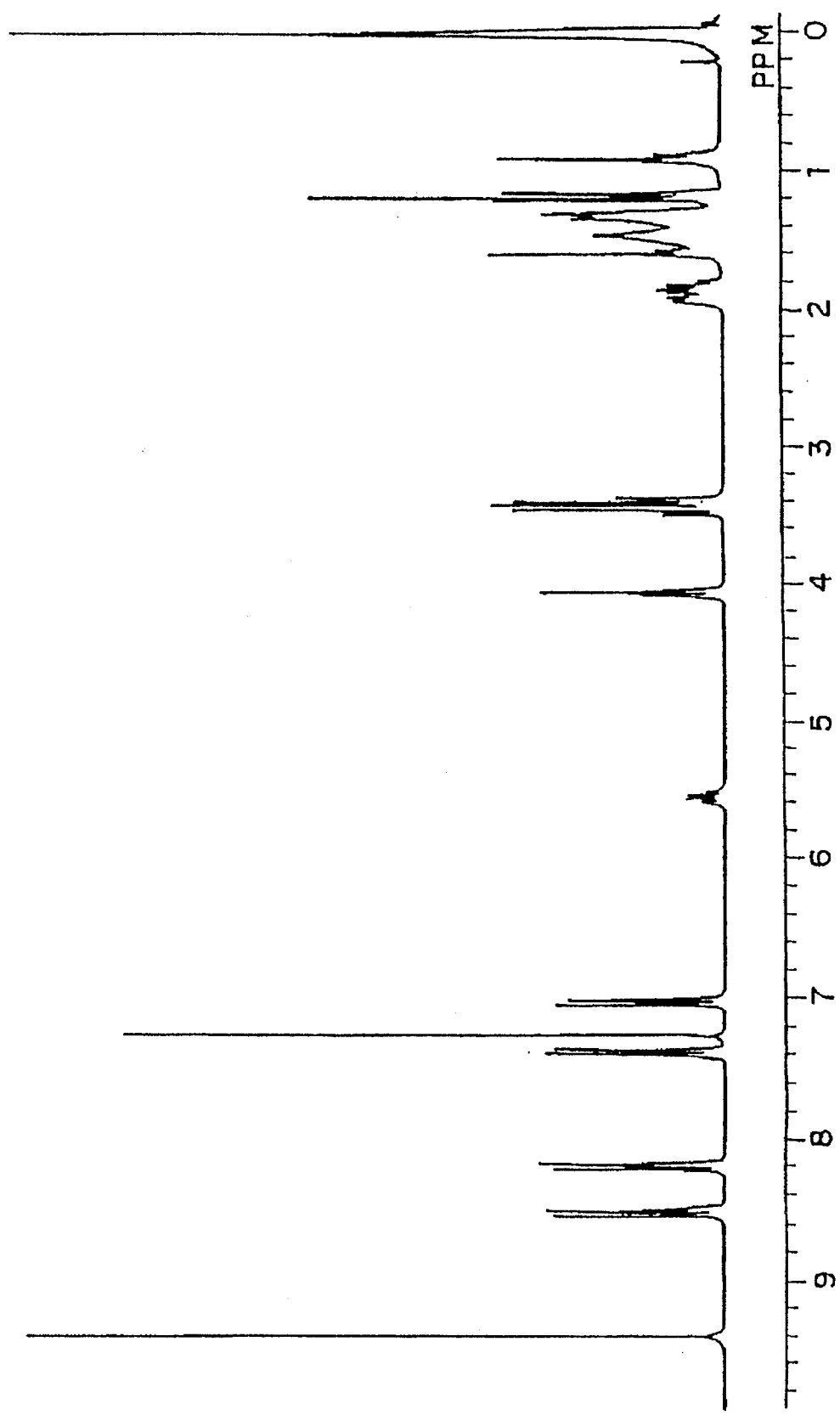
FIG. 5 is a drawing showing the NMR spectrum of the liquid crystal substance obtained in Example 4.
Figure 6:
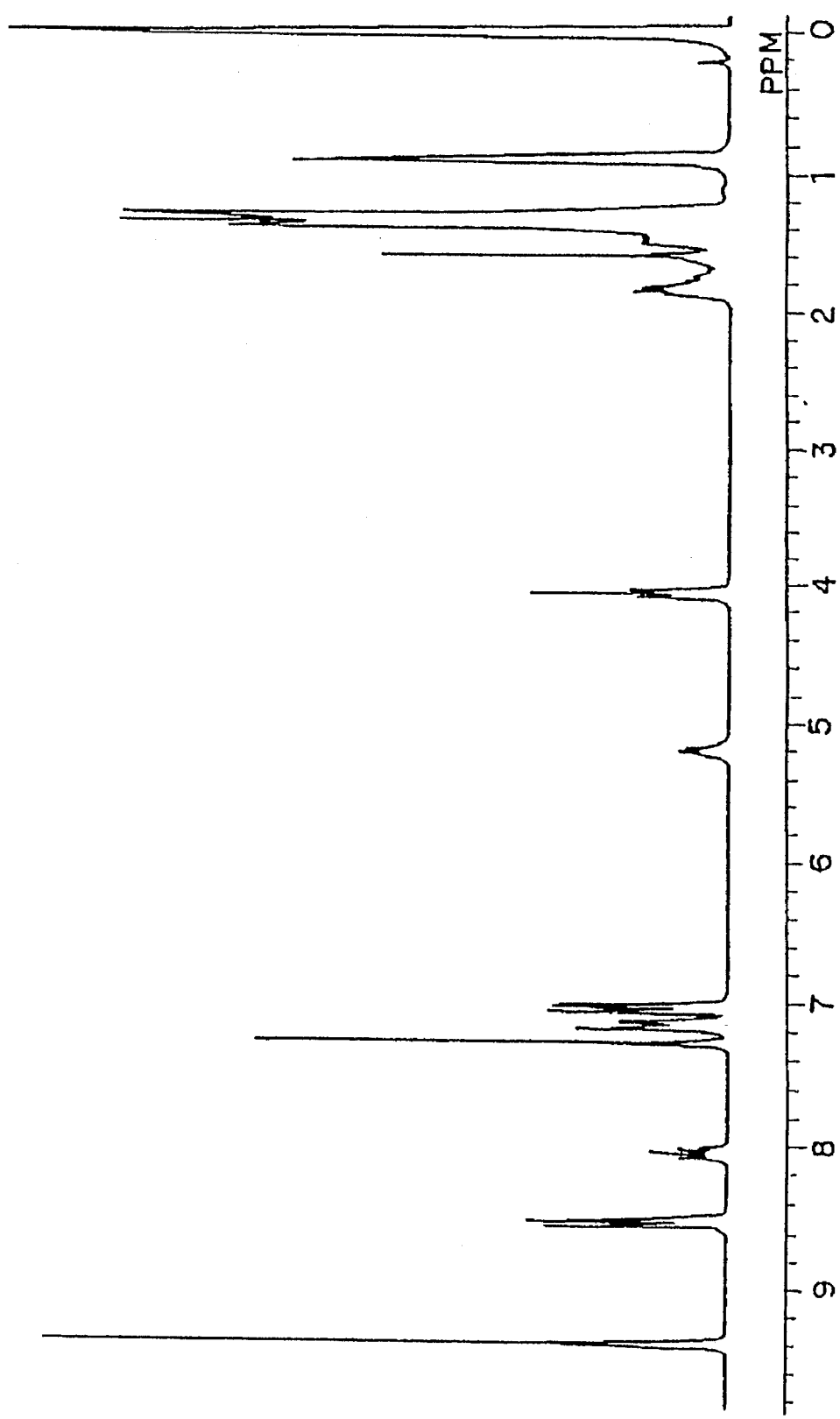
FIG. 6 is a drawing showing the NMR spectrum of the liquid crystal substance obtained in Example 5.
Figure 7:
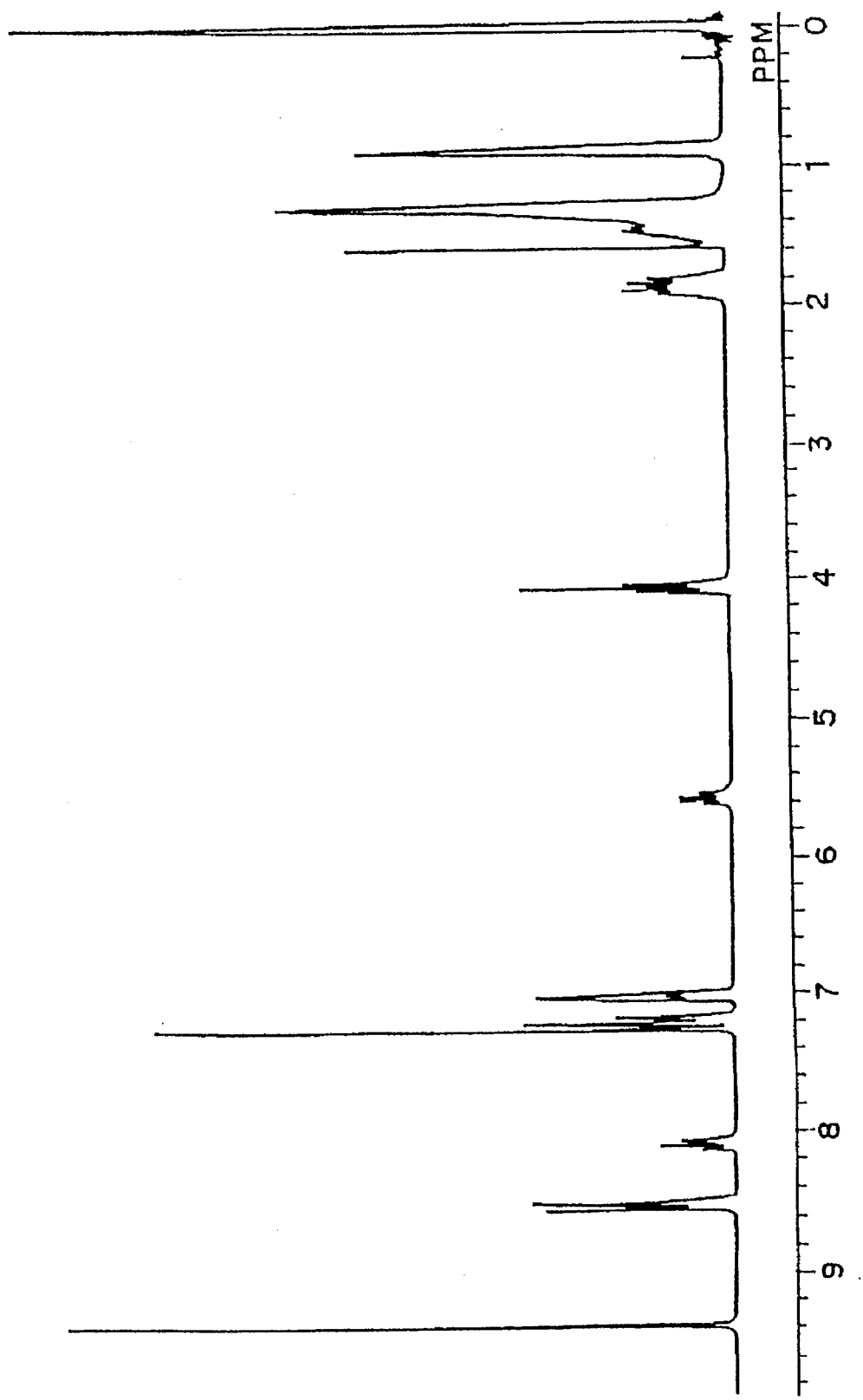
FIG. 7 is a drawing showing the NMR spectrum of the liquid crystal substance obtained in Example 6.
Figure 8:
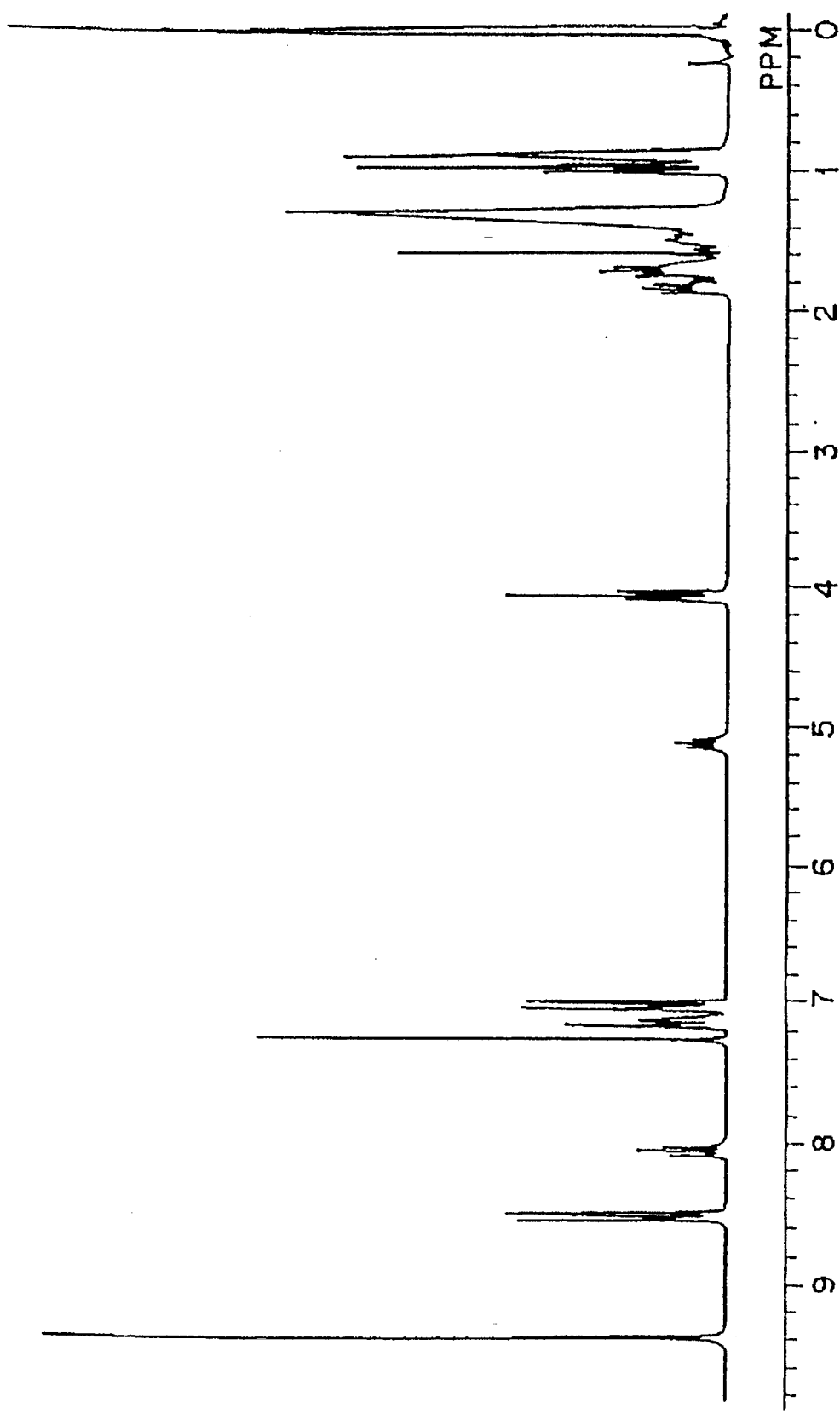
FIG. 8 is a drawing showing the NMR spectrum of the liquid crystal substance obtained in Example 7.
Figure 9:
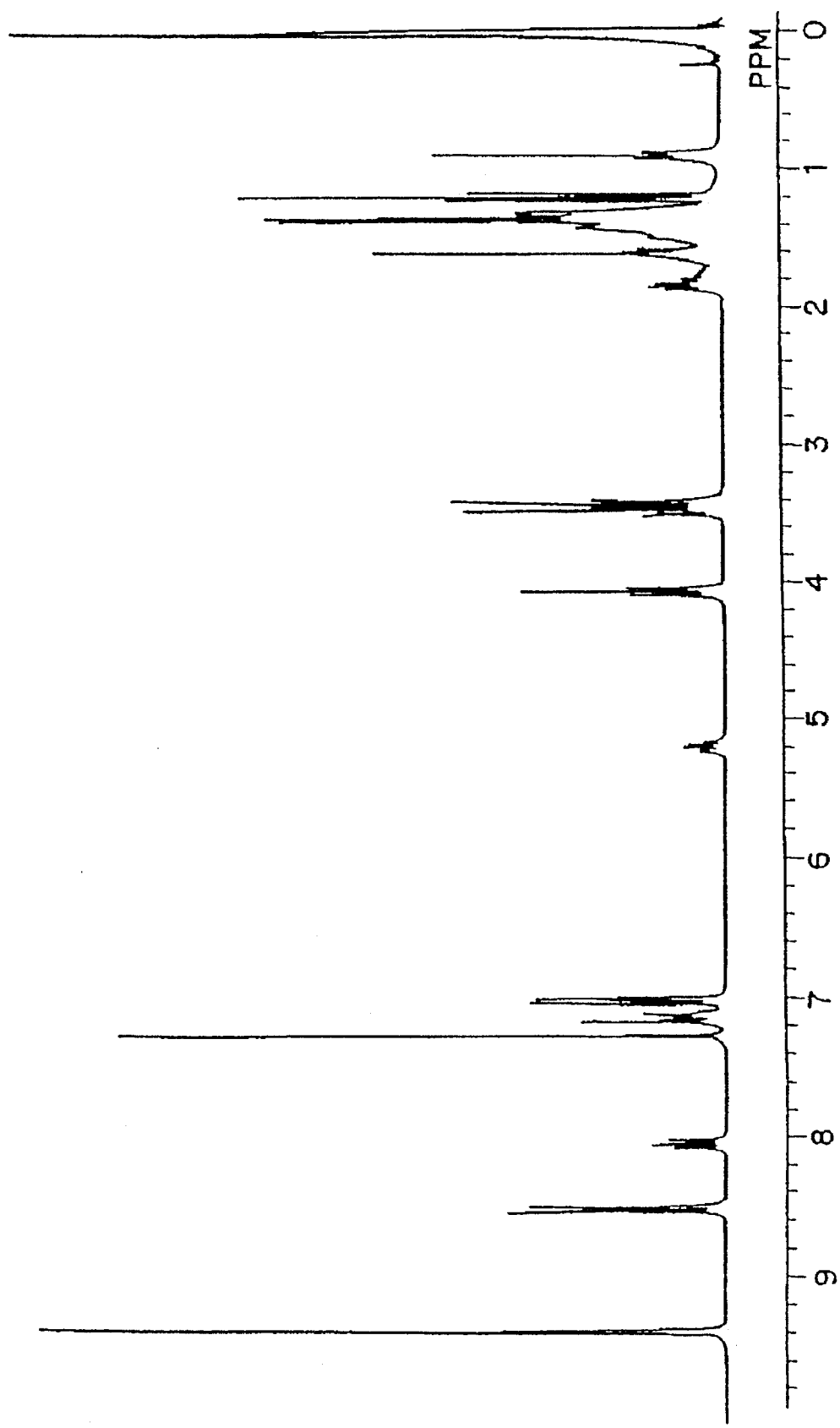
FIG. 9 is a drawing showing the NMR spectrum of the liquid crystal substance obtained in Example 8.
Figure 10:
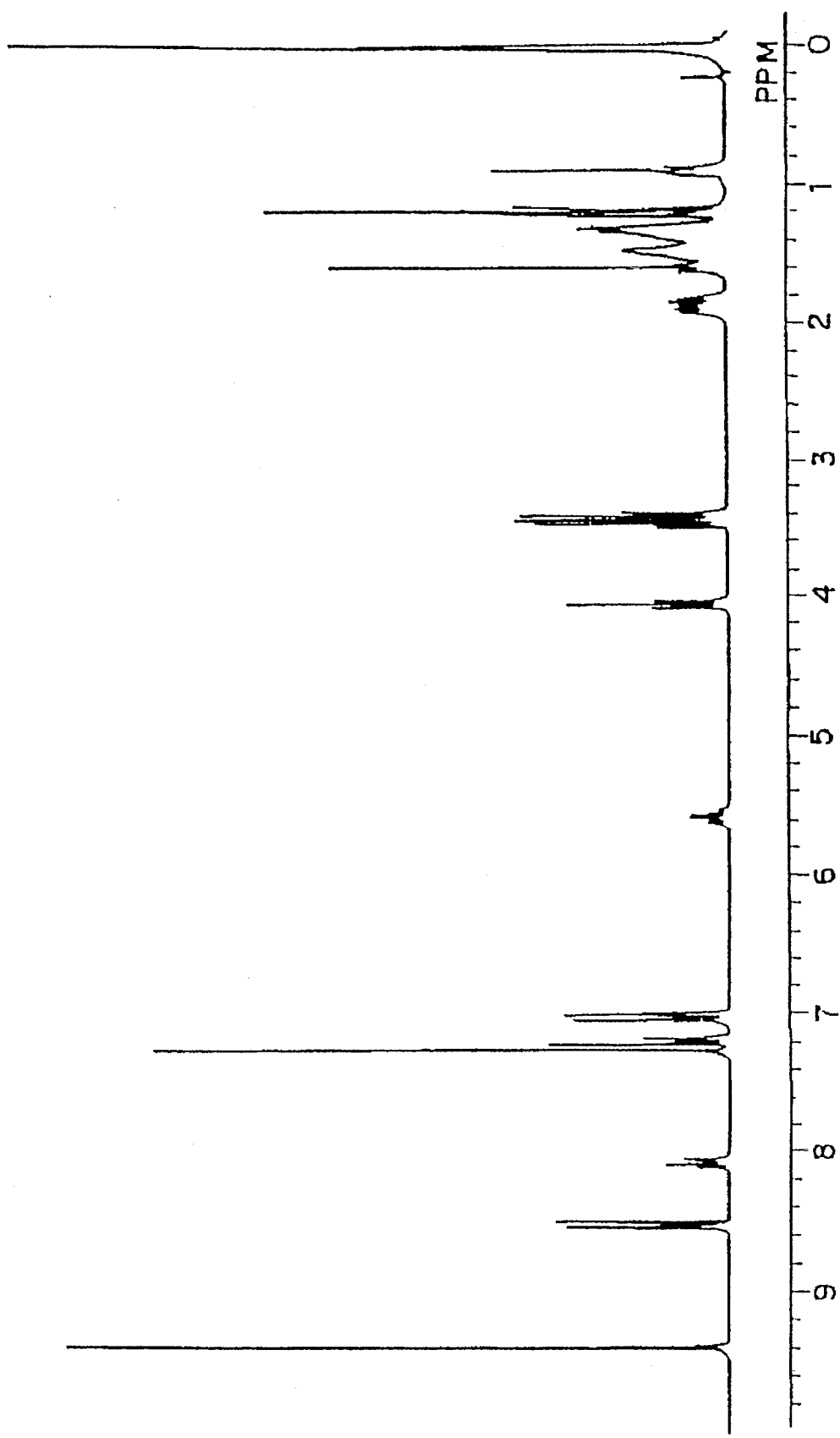
FIG. 10 is a drawing showing the NMR spectrum of the liquid crystal substance obtained in Example 9.
Figure 11:
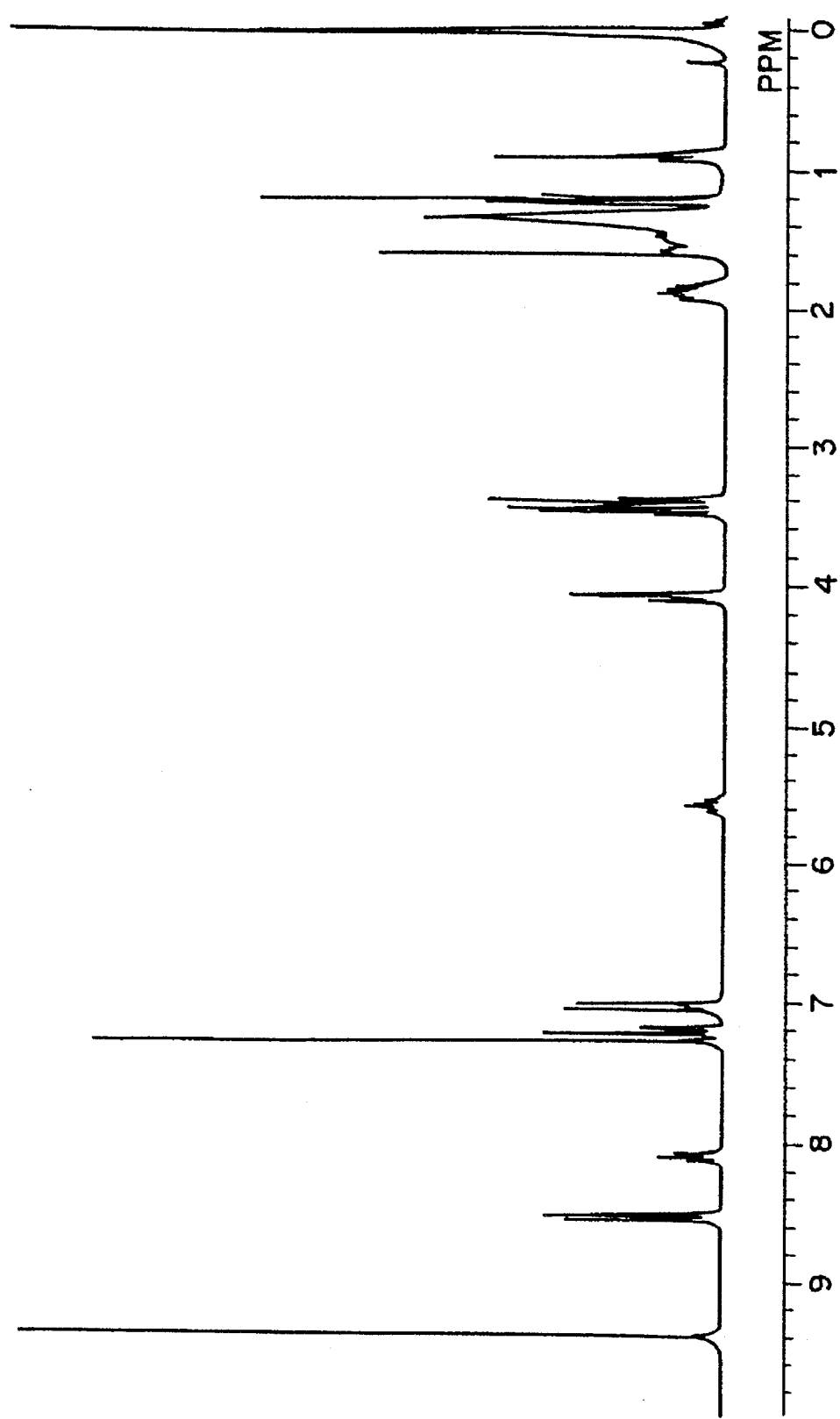
FIG. 11 is a drawing showing the NMR spectrum of the liquid crystal substance obtained in Example 10.

Example 1 was repeated except that (R)-4-hydroxy-1-(1-methylpentyloxycarbonyl)benzene was replaced by (R)-4-hydroxy-1-(1methylheptyloxycarbonyl)benzene (Example 2), or (S)-4- hydroxy-(1-methyl-6-ethoxy-hexyloxycarbonyl)benzene (Example 3), or (R)-4-hydroxy-1-(1-trifluoromethyl-6-ethoxyhexyloxycarbonyl)benzene (Example 4), to produce, respectively, 4-(1-methylheptyloxyhydroxycarbonyl)-phenyl ester of 2-(4-octyloxyphenyl)-5pyrimidinecarboxylic acid (Example 2), 4-(1-methyl-6ethoxyhexyloxycarbonyl)phenyl ester of 2-(4-octyloxyphenyl)-5-pyrimidinecarboxylic acid (Example 3) and 4-(1-trifluoromethyl-6-ethoxyhexyloxycarbonyl)phenyl ester of 2 -(4-octyloxyphenyl)-5-pyrimidinecarboxylic acid (Example 4). NMR spectra of those compounds a re shown as FIGS. 3, 4 and 5, respectively. When phase sequences of these compounds were measured in the same manner as in Example 1, the results as shown in Table 1 were obtained, indicating that they all possess anti-ferroelectric phase.

Crystal $\xleftarrow{96°\text{ C.}}$ SCA $\xleftarrow{120°\text{ C.}}$ SC $\xleftarrow{122°\text{ C.}}$ SA $\xleftarrow{135°\text{ C.}}$ isotropic phase In the above, SA means smectic A phase, SC, chiralsmectic C phase, and SCA, anti-ferroelectric phase.

TABLE 1

Phase sequences of the compounds of Examples 2 to 4

| Ex. No. | Structure of optically active moiety | Phase sequence |
|---|---|---|
| 2 | —CH(CH$_3$)C$_6$H$_{13}$ | Crystal $\xleftarrow{96°\text{ C.}}$ SCA $\xleftarrow{99°\text{ C.}}$ SC** $\xleftarrow{111°\text{ C.}}$ SA $\xleftarrow{127°\text{ C.}}$ isotropic phase |

TABLE 1-continued

| | | Phase sequences of the compounds of Examples 2 to 4 |
|---|---|---|
| Ex. No. | Structure of optically active moiety | Phase sequence |
| 3 | $-C^{}H(CH_3)(CH_2)_5OC_2H_5$ | Crystal $\xrightarrow{72°\,C.}$ SCA $\xrightarrow{83°\,C.}$ SA $\xrightarrow{108°\,C.}$ isotropic phase |
| 4 | $-C^{}H(CF_3)(CH_2)_5OC_2H_5$ | Crystal $\xrightarrow{48°\,C.}$ SCA $\xrightarrow{74°\,C.}$ SC** $\xrightarrow{75°\,C.}$ SA $\xrightarrow{92°\,C.}$ isotropic phase |

Contrast ratios were measured in the same manner as in Example 1, with the results as shown in Table 2 below.

TABLE 2

| Contrast Ratios in Examples 2 to 4 | | |
|---|---|---|
| Example No. | Measuring temp. | Contrast ratio |
| 2 | anti-ferroelectric phase range was too narrow for the measurement | |
| 3 | 70° C. | 15 |
| 4 | 55° C. | 14 |

Examples 5 to 10

Example 1 was repeated except that the optically active moiety of the compounds of the formula (1), in which R is $C_8H_{17}$ and X is F, was varied for each run to prepare liquid crystal substances.

The NMR spectra of the resultant compounds are as shown in FIGS. 6, 7, 8, 9, 10 and 11. Also the phase sequences of these compounds were measured in the same manner as in Example 1, with the results as shown in Table 3 below. All of the compounds had an anti-ferroelectric phase.

Their contrast ratios were measured in the same manner as in Example 1, with the results as shown in Table 4 below.

TABLE 4

| Contrast Ratios in Examples 5 to 10 | | |
|---|---|---|
| Example No. | Measuring temp. (°C.) | Contrast ratio |
| 5 | 90 | 13 |
| 6 | 60 | 13 |
| 7 | 80 | 14 |
| 8 | 90 | 12 |
| 9 | 50 | 13 |
| 10 | 45 | 13 |

Comparative Examples 1 to 3

Example 1 was repeated except that the fluorine-substituted site in the liquid crystal substances formed in Examples 5 to 10 was changed as in the formula below:

TABLE 3

| | | Phase sequences of the compounds of Examples 5 to 10 |
|---|---|---|
| Ex. No. | Structure of optically active moiety | Phase sequence |
| 5 | $-C^{}H(CH_3)C_6H_{13}$ | Crystal $\xrightarrow{70°\,C.}$ SCA $\xrightarrow{123°\,C.}$ SA $\xrightarrow{135°\,C.}$ isotropic phase |
| 6 | $-C^{}H(CF_3)C_6H_{13}$ | Crystal $\xrightarrow{54°\,C.}$ SCA $\xrightarrow{101°\,C.}$ SA $\xrightarrow{110°\,C.}$ isotropic phase |
| 7 | $-C^{}H(C_2H_5)C_6H_{13}$ | Crystal $\xrightarrow{50°\,C.}$ SCA $\xrightarrow{90°\,C.}$ SA $\xrightarrow{92°\,C.}$ isotropic phase |
| 8 | $-C^{*}H(CH_3)(CH_2)_5OC_2H_5$ | Crystal $\xrightarrow{78°\,C.}$ SCA** $\xrightarrow{103°\,C.}$ SA $\xrightarrow{121°\,C.}$ isotropic phase |
| 9 | $-C^{*}H(CF_3)(CH_2)_5OC_2H_5$ | Crystal $\xrightarrow{41°\,C.}$ SCA** $\xrightarrow{80°\,C.}$ isotropic phase |
| 10 | $-C^{*}H(CF_3)(CH_2)_7OC_2H_5$ | Crystal $\xrightarrow{33°\,C.}$ SCA** $\xrightarrow{71°\,C.}$ SA $\xrightarrow{74°\,C.}$ isotropic phase |

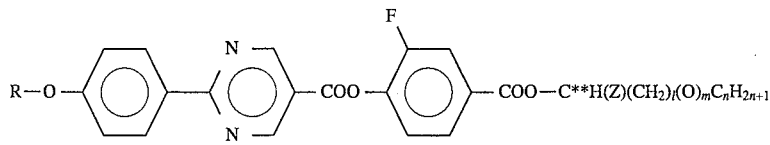

in which R is $C_8H_{17}$, and that the optically active moiety was changed for each run to prepare liquid crystal substances.

Figure 12:
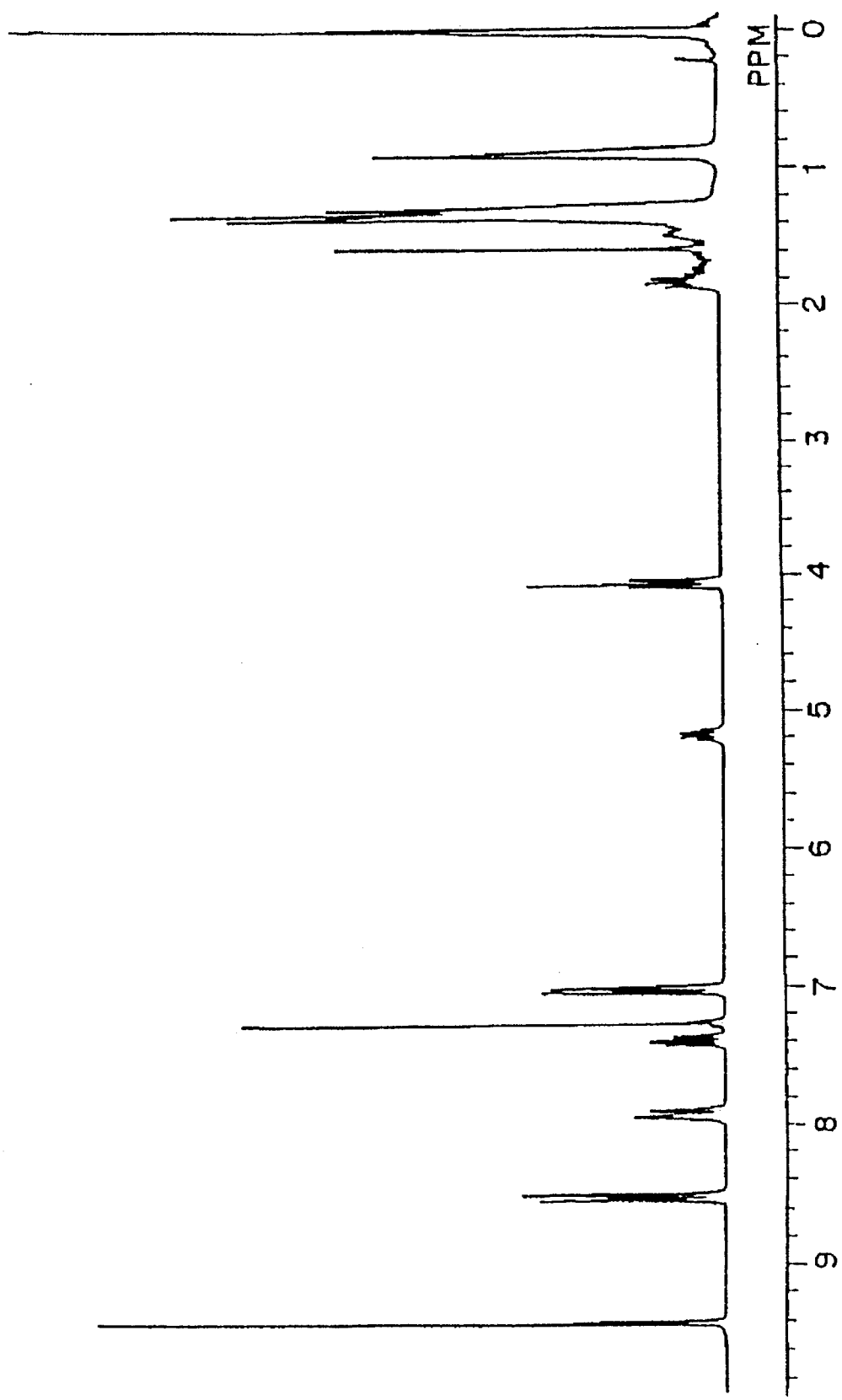
FIG. 12 is a drawing showing the NMR spectrum of the liquid crystal substance obtained in Comparative Example 1.
Figure 13:
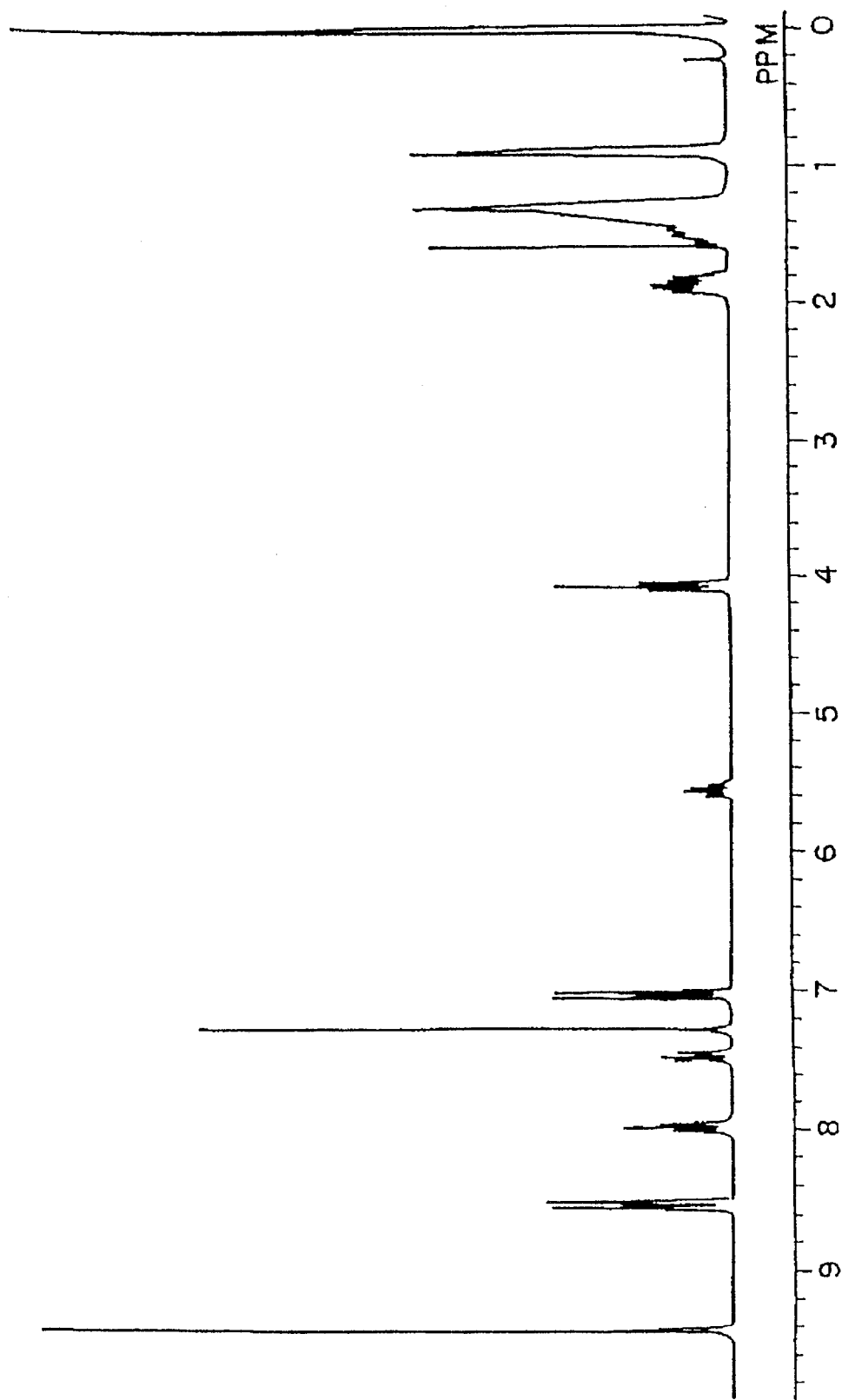
FIG. 13 is a drawing showing the NMR spectrum of the liquid crystal substance obtained in Comparative Example 2.
Figure 14:
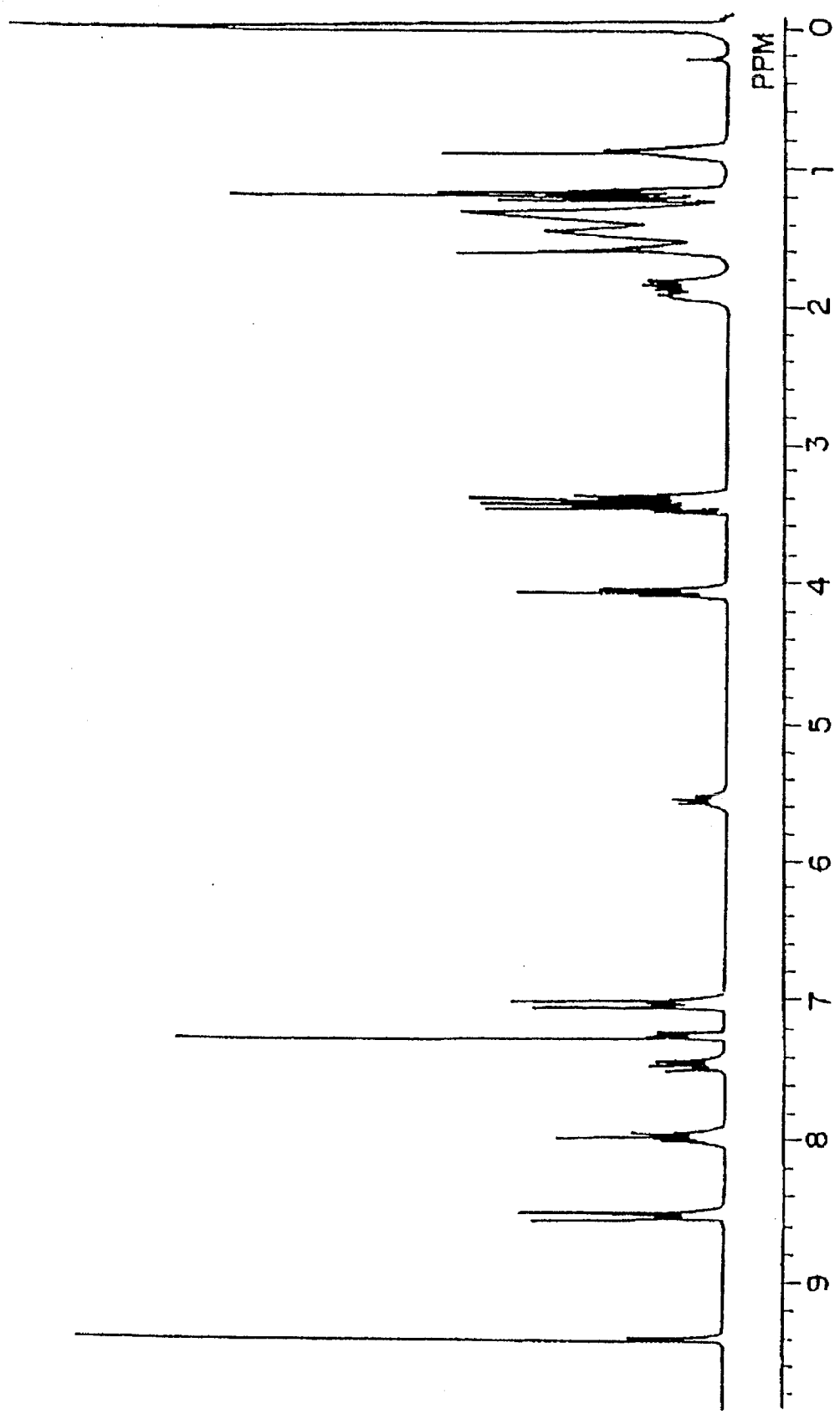
FIG. 14 is a drawing showing the NMR spectrum of the liquid crystal substance obtained in Comparative Example 3.
Figure 15:
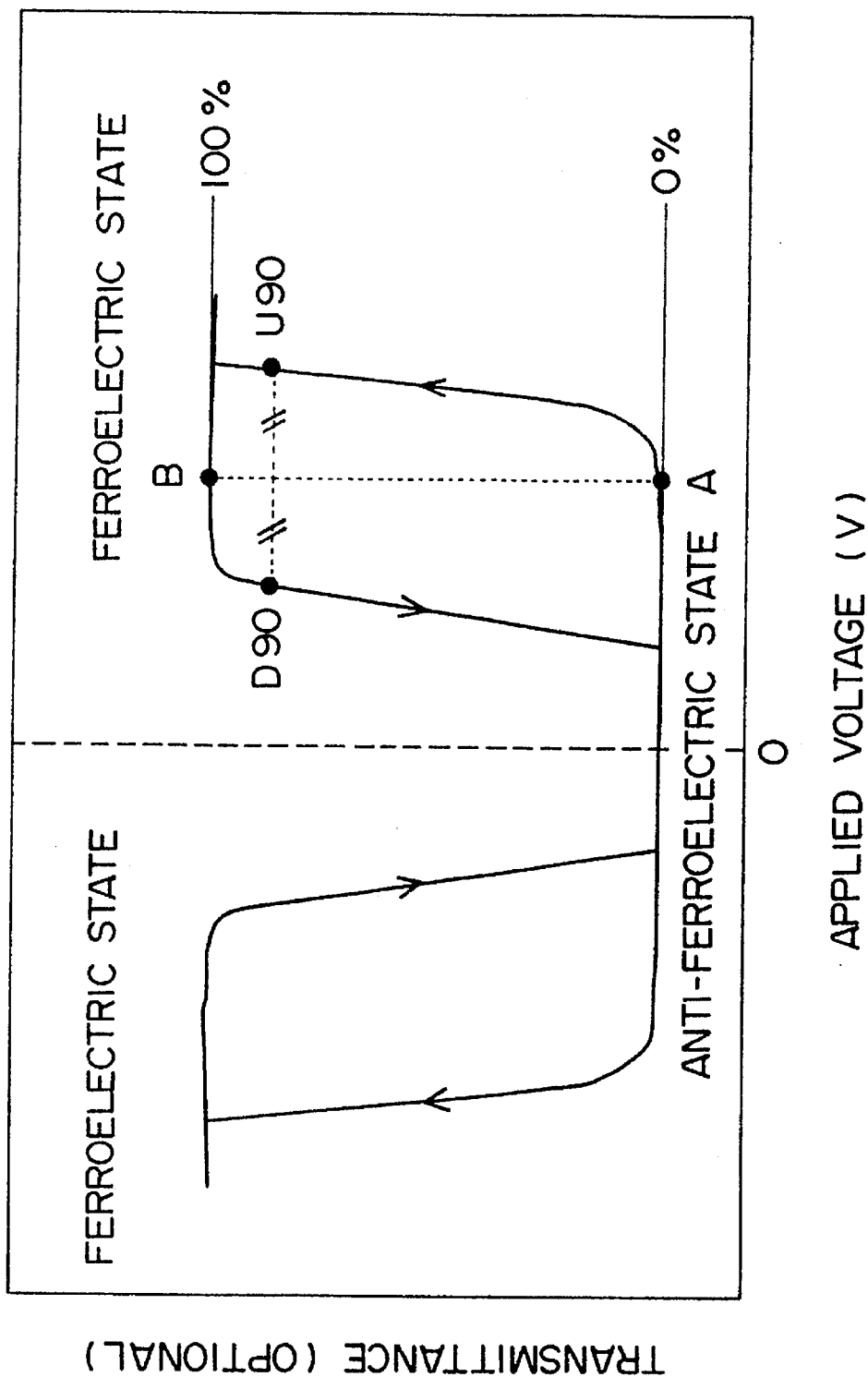
FIG. 15 is a drawing to explain how the contrast ratio is determined.

NMR spectra of the produced substances are shown as FIGS. 12, 13 and 14, respectively. When their phase sequences were measured in the same manner as in Example 1, the results shown in the following Table 5 were obtained. In none of them presence of anti-ferroelectric phase was recognized.

TABLE 5

Phase sequences of the compounds of Comparative Examples 1 to 3

| Comparative Example No. | Structure of optically active moiety | Phase sequence |
|---|---|---|
| 1 | $-C^{**}H(CH_3)C_6H_{13}$ | Crystal ⇌ 84° C. SA ⇌ 92° C. isotropic phase |
| 2 | $-C^{**}H(CF_3)C_6H_{13}$ | Crystal ⇌ 69° C. SA ⇌ 90° C. isotropic phase |
| 3 | $-C^{**}H(CF_3)(CH_2)_5OC_2H_5$ | Crystal ⇌ 48° C. SA ⇌ 83° C. isotropic phase |

We claim:

1. Liquid crystal substances which are represented by the formula (1):

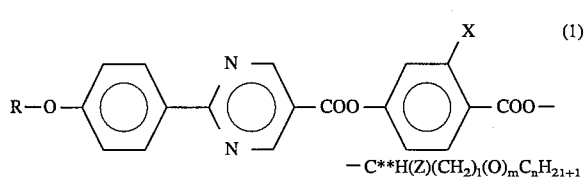

wherein
R is a straight chain alkyl group having 6 to 10 carbon atoms,
X is hydrogen or fluorine atom,
Z is [—$CF_3$, ]—$CF_3$, [or—$C_2H_5$,] and
C** stands for an asymmetric carbon atom, and
l is an integer of 5 to 7, m is 1 and n is 2.

2. Liquid crystal substances represented by the formula (1) as defined in claim 1, in which R is a straight chain alkyl group having 8 carbon atoms.

3. A liquid crystal display device comprising the liquid crystal substances of claim 1 or 2.

4. Liquid crystal substances which are represented by the formula (1):

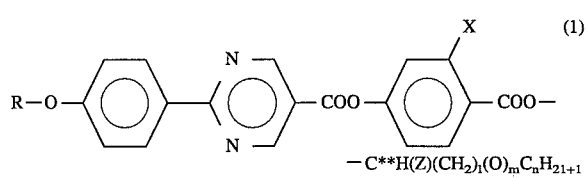

wherein
R is a straight chain alkyl group having 6 to 10 carbon atoms,
X is hydrogen,
Z is —$CF_3$, and
C** stands for an asymmetric carbon atom, and
l is an integer of 5 to 7, m is 1 and n is 2.

5. Liquid crystal substances represented by the formula (1) as defined in claim 4, in which R is a straight chain alkyl group having 8 carbon atoms.

6. A liquid crystal display device comprising the liquid crystal substance of claim 4 or 5.

7. Liquid crystal substances which are represented by the formula (1):

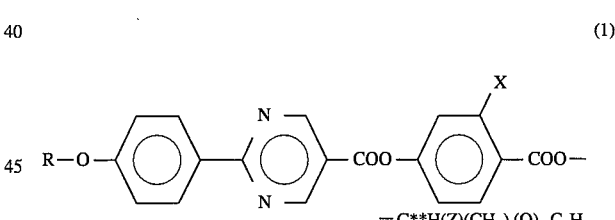

wherein
R is a straight chain alkyl group having 6 to 10 carbon atoms,
X is fluorine atom,
Z is —$CF_3$, and
C** stands for an asymmetric carbon atom, and
l is an integer of 5 to 7, m is 1 and n is 2.

8. Liquid crystal substances represented by the formula (1) as defined in claim 7, in which R is a straight chain alkyl group having 8 carbon atoms.

9. A liquid crystal display device comprising the liquid crystal substances of claim 7 or 8.

* * * * *